United States Patent [19]

Eden

[11] Patent Number: 5,022,401

[45] Date of Patent: Jun. 11, 1991

[54] APPARATUS FOR POSITIONING A MEASURING ELEMENT

[75] Inventor: Alec Eden, Überlingen, Fed. Rep. of Germany

[73] Assignee: Eden Medizinische Elektronik GmbH, Überlingen, Fed. Rep. of Germany

[21] Appl. No.: 466,045

[22] Filed: Jan. 17, 1990

[30] Foreign Application Priority Data

Jul. 4, 1989 [DE] Fed. Rep. of Germany ....... 3921957

[51] Int. Cl.⁵ ............................................. A61B 10/00
[52] U.S. Cl. ................................................ 128/662.03
[58] Field of Search ...................... 128/661.08, 661.09, 128/661.10, 662.01, 662.03, 662.04; 73/861.25, 861.26, 861.28

[56] References Cited

U.S. PATENT DOCUMENTS

| | | | |
|---|---|---|---|
| 4,421,118 | 12/1983 | Dow et al. | 128/660.1 |
| 4,601,292 | 7/1986 | Fidel et al. | 128/662.04 |
| 4,817,621 | 4/1989 | Aaslid | 128/662.03 |

Primary Examiner—William E. Kamm
Assistant Examiner—Kevin Pontius
Attorney, Agent, or Firm—Robert W. Becker & Associates

[57] ABSTRACT

An apparatus for positioning a measuring element that is pivotably mounted, via two parallelogram-type linkage systems that are disposed at an angle to one another, in such a way as to be movable in a random fashion. The free ends of the lever arms of the two linkage systems are respectively supported on a common carrier plate via the intervention of a respective pivotably mounted intermediate member.

13 Claims, 2 Drawing Sheets

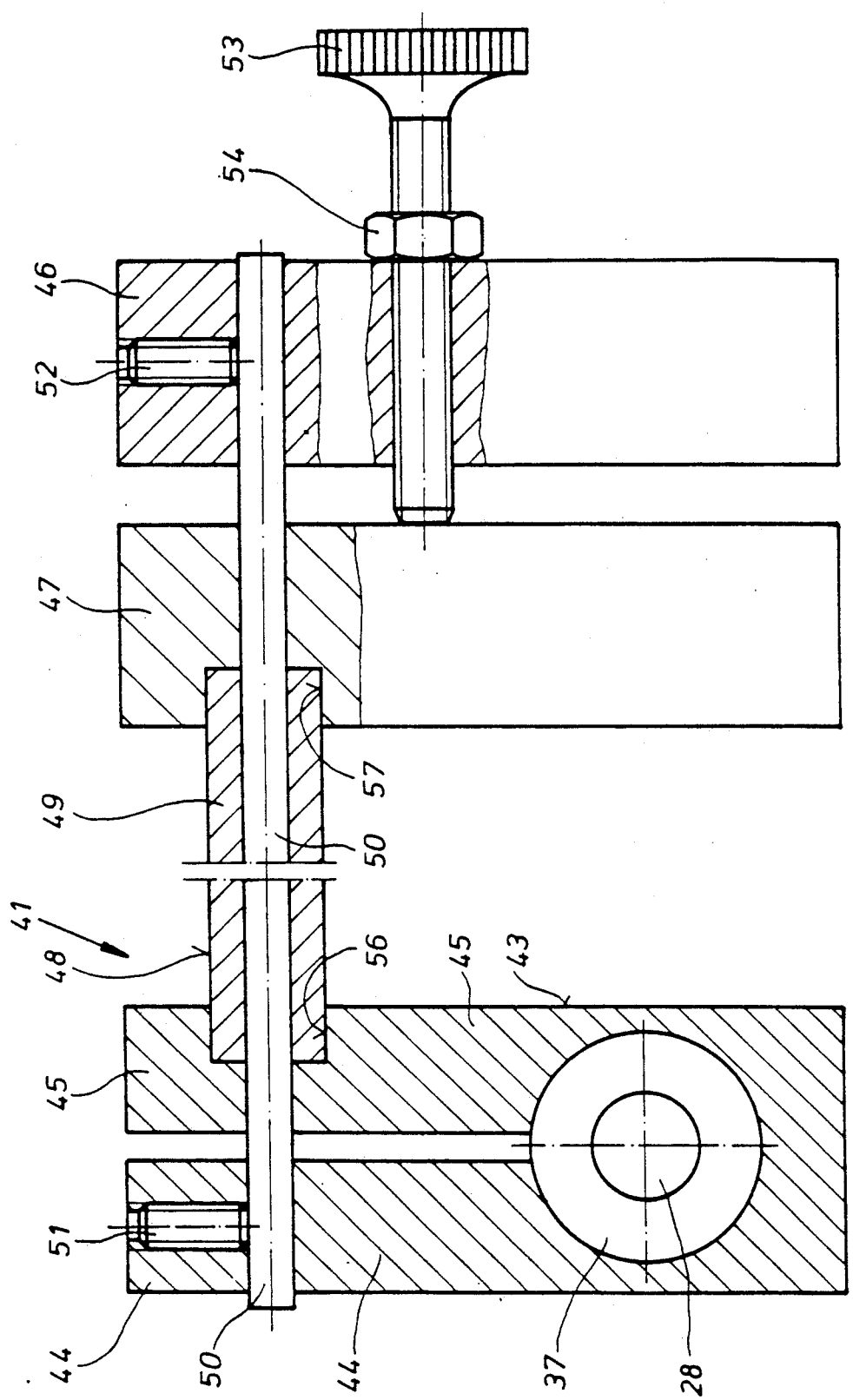

APPARATUS FOR POSITIONING A MEASURING ELEMENT

BACKGROUND OF THE INVENTION

The present invention relates to an apparatus for positioning a measuring element, for example a Doppler signal emitter or receiver, for determining the position of a blood vessel and/or the direction in which the blood flows in this blood vessel, with the measuring element being pivotably mounted, via two parallelogram-type linkage systems that are disposed at an angle to one another, in such a way as to be movable in a random fashion.

U.S. Pat. No. 4,817,621, Rune Aaslid, dated Apr, 4, 1989, which is owned by the assignee of the present application, discloses an apparatus of this general type. In this known apparatus, the free ends of the parallelogram-type linkage systems are each pivotably held on a respective reference plate, with these plates being disposed at a given angle to one another. When a patient is being examined with this known apparatus, the reference plates are placed directly against the head of the patient at predetermined locations. Although this heretofore known apparatus functions satisfactorily, the capital expenditure for such an apparatus is considerable, especially due to the large number of linkages that are required. This known apparatus is therefore not economical to manufacture. Disruptions must also be taken into consideration since the measuring element does not maintain its assumed position. A further drawback is that examinations can be conducted only when the patient is in a horizontal position, and cannot be carried out at all locations of the head. In addition, handling of the apparatus is difficult, again due to the considerable weight of the apparatus. Furthermore, a patient should not move his head when an examination is being conducted with this known apparatus, since this can lead to incorrect results, and the position of the measuring element would have to be corrected.

It is therefore an object of the present invention to provide an apparatus of the aforementioned general type for positioning a measuring element, with the novel apparatus having an extremely straightforward construction and hence being economical to manufacture and enabling a disruption-free manner of operation. However, a primary object is that the measuring element be easy to position and that it reliably remain in the assumed position, so that examinations can be carried out over a long period of time without having to undergo corrections. In addition, it should be possible to effect such examinations in nearly every position of the patient, especially in a sitting position, and it should be possible to secure the apparatus, without difficulty, on a head carrier, so that movements of the head will not adversely affect the positioning of the measuring element.

BRIEF DESCRIPTION OF THE DRAWINGS

These and other objects and advantages of the present invention will appear more clearly from the following specification in conjunction with the accompanying schematic drawings, in which:

FIG. 2 is a cross-sectional view through the arresting mechanism that is associated with the apparatus of FIG. 1.

SUMMARY OF THE INVENTION

Figure 1:
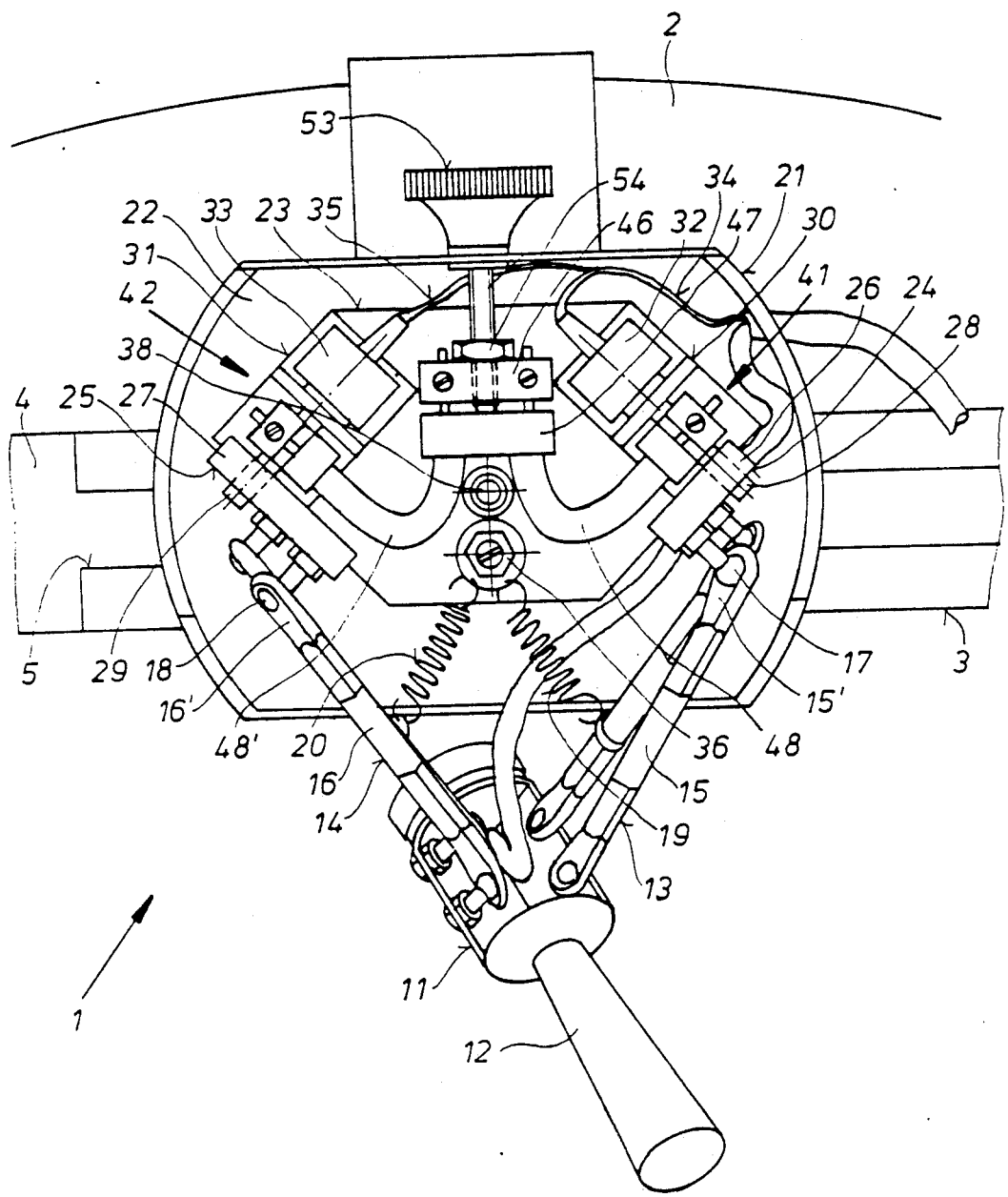
FIG. 1 is a plan view of one exemplary embodiment of the inventive apparatus, which is secured on the head of a patient and is disposed in a housing.

The apparatus of the present invention is characterized primarily in that the free ends of the lever arms of the parallelogram-type linkage systems are supported on a common carrier plate via the intervention of a respective pivotably mounted intermediate member.

In this connection, it is very advantageous to associate with each of the intermediate members a respective arresting mechanism, with these arresting mechanisms advantageously being actuatable together.

It is furthermore suitable to embody each of the intermediate members as a plate that is mounted on a rotatable shaft, and in which the free ends of the lever arms of the linkage systems are pivotably supported via ball-and-socket joints or the like, whereby to determine the position of the measuring elements, each of the shafts should be connected with a potentiometer via which the rotational movements of the shafts can be measured.

For the support of the measuring element, for example on the head of a patient, it is proposed pursuant to a further embodiment of the present invention that at least one of the lever arms of each of the linkage systems be supported on the carrier plate, or on a housing that accommodates the same, via a tension spring.

In order to make it possible to have a straightforward construction, the arresting mechanisms should be associated with the shafts that carry the intermediate members, whereby each of the arresting mechanisms is formed by a dual-arm arresting shoe that extends about the shaft, with the arresting shoes preferably being able to carry out a tightening action together via tensioning or cable means.

Pursuant to one specific embodiment of the present invention, the tensioning means of the arresting mechanisms, and hence the arresting force, are supported via an abutment that is fixedly mounted on the carrier plate and can be shifted via a tightening screw, whereby the shifting path should be capable of being adjusted via a stop means, for example in the form of a nut, that is disposed on the tightening screw and cooperates with the abutment.

With the inventive apparatus for positioning a measuring element, not only is a very straightforward construction and hence economical manufacture provided, but the novel apparatus is also easy to handle and can be easily secured without difficulty directly on the head of a patient via a head carrier, for example in the form of a head band. This is accomplished because if the parallelogram-type linkage systems are supported on a common carrier plate via a respective pivotable intermediate member, all of the components of the apparatus can be compactly accommodated in a housing that is easy to secure and adjust and that to a certain extent forms a reference plate.

As a result, examinations can be carried out in nearly every position of the patient, especially in a sitting position, and movements of the head do not have an adverse effect upon the examination, especially since the measuring element can be easily maintained in the aligned position with the aid of the arresting mechanisms; consequently, examinations can be readily carried out over a long period of time. Due to the easy handling, a reliable and disruption free manner of operation is provided.

Further specific features of the present invention will be described in detail subsequently.

DESCRIPTION OF PREFERRED EMBODIMENTS

Referring now to the drawings in detail, the apparatus 1 illustrated in FIG. 1 serves for the positioning of a measuring element 11 on the head 2 of a patient, for example in order to determine the position of a blood vessel and/or the direction in which the blood flows in this vessel. The apparatus is held via a head carrier 3 that is in the form of a band 4, which is provided with a carriage guide 5; the apparatus 1 is thereby easily adjustable over a large portion of the head 2.

The measuring element 11, which is provided with a handle 12, via two parallelogram-type linkage systems 13 and 14 that are disposed at an angle to one another, is pivotably mounted in such a way as to be movable in a random fashion, and in particular is mounted on a carrier plate 23 that is secured to a base plate 22 of a housing 21. With the aid of a non-illustrated clamping bolt that extends through the central bore 38, the housing 21 can be easily secured with the carriage guide 5 of the carrier 3 once the measuring element 11 has been positioned.

Respective intermediate members 24 and 25, which are embodied as the plates 26 and 27, are provided for the pivotable mounting of the two parallelogram-type linkage systems 13 and 14. The free ends 15' and 16' of the lever arms 15 and 16 of the parallelogram-type linkage systems 13 and 14 are connected to the plates 26 and 27 via ball-and-socket joints 17 and 18. In addition, the intermediate members 24 and 25 are disposed on shafts 28 and 29 that are rotatably held in bearing holders 30 and 31 that are secured to the carrier plate 23. Since the shafts 28 and 29 are connected to potentiometers 32 and 33 via which the rotational movements of the shafts 28 and 29 can be measured, signals that correspond to the position of the measuring element 11 can be generated and delivered via the lines 34 and 35.

So that the measuring element 11 always rests upon the head 2 of the patient, a respective tension spring 19 or 20 acts upon each of the lever arms 15 and 16 of the parallelogram-type linkage systems 13 and 14; by means of a bolt 36, the tension springs 19 and 20 are similarly mounted on the carrier plate 23. The measuring element 11 is therefore always pulled in the direction toward the head 2.

Furthermore associated with the intermediate members 24 and 25, and hence with the parallelogram-type linkage systems 13 and 14, are arresting mechanisms 41 and 42 for fixing the same, so that the measuring element 11 will remain in a position that it has assumed and can undertake tests over a longer period of time.

The arresting mechanisms 41 and 42 cooperate with the shafts 28 and 29 and, as can be seen in particular in FIG. 2, each comprising a dual-arm arresting shoe 43, the arms 44 and 45 of which extend about a sleeve 37 that has been pressed or shrunk onto the shaft 28 or 29. By means of tensioning or cable means 48 and 48', the arresting mechanisms 41 and 42 can be actuated together.

In order to be able to realize this, an abutment 46 is fixedly disposed on the carrier plate 23, and the tensioning or cable means 48, 48', which comprise a sheathing 49 and a tensioning member 50, are supported on the arresting shoes 43 and a crosspiece 47, which is adjustable via a tightening screw 53. In this connection, the tensioning members 50 are secured to the arm 44 or the abutment 46 by screws 51 and 52, while the sheathings 49 are guided in a bore 56 of the arm 45 and a bore 57 of the crosspiece 47. If, after positioning of the measuring element 11, the crosspiece 47 is shifted via the tightening screw 53 in a direction toward the arresting shoe 43, the shifting movement of which is transmitted to the arm 45 via the sheathing 49 of the tensioning or cable means 48, 48', the arresting shoes 43 are pressed together and the shafts 28 and 29, i.e. the sleeves 37 that are connected therewith, are thereby secured, so that depending upon the arresting force that has been exerted, shifting movements of the parallelogram-type linkage systems 13 and 14, and hence of the measuring element 11, are nearly precluded. So that the arresting force can be adjusted, a stop means in the form of a nut 54 is disposed on the tightening screw 53. By resting against the abutment 46, this nut 54 limits the shifting movement of the tightening screw 53.

The present invention is, of course, in no way restricted to the specific disclosure of the specification and drawings, but also encompasses any modifications within the scope of the appended claims.

What I claim is:

1. In an apparatus for positioning a measuring element, such as a Doppler signal emitter or receiver, for determining the position of a blood vessel and/or the direction in which the blood flows in this blood vessel, with said measuring element being pivotably mounted, via two parallelogram-type linkage systems that are disposed at an angle to one another, in such a way as to be movable in a random manner, the improvement wherein:

said linkage systems have lever arms free ends that are respectively supported on a common carrier plate including a respective pivotably mounted intermediate member therewith;

a respective arresting mechanism is operatively associated with each of said intermediate members; and means for actuating said arresting mechanisms separately.

2. In an apparatus for positioning a measuring element, such as a Doppler signal emitter or receiver, for determining the position of a blood vessel and/or the direction in which the blood flows in this blood vessel, with said measuring element being pivotably mounted, via two parallelogram-type linkage systems that are disposed at an angle to one another, in such a way as to be movable in a random manner, the improvement wherein:

said linkage systems have lever arms with free ends that are respectively supported on a common carrier plate including a respective pivotably mounted intermediate member therewith;

a respective arresting mechanism is operatively associated with each of said intermediate members; and means for actuating said arresting mechanisms together.

3. An apparatus according to claim 2, in which each of said intermediate members is in the form of a plate-like member that is mounted on a respective shaft that in turn is rotatably mounted on said carrier plate; and in which said free ends of said lever arms of said linkage systems are pivotably supported on said plate-like members.

4. An apparatus according to claim 3, in which said pivotable support of said free ends of said lever arms includes ball-and-socket joints therewith.

5. An apparatus according to claim 3, in which to facilitate engagement of said measuring element, for example against the head of a patient, at least one of said lever arms of said linkage systems is operatively connected via a respective tension spring to said carrier plate to a housing that accommodates same.

6. In an apparatus for positioning a measuring element, such as a Doppler signal emitter or receiver, for determining the position of a blood vessel and/or the direction in which the blood flows in this blood vessel, with said measuring element being pivotably mounted, via two parallelogram-type linkage systems that are disposed at an angle to one another, in such a way as to be movable in a random manner, the improvement wherein:

said linkage systems have lever arms with free ends that are respectively supported on a common carrier plate including a respective pivotably mounted intermediate member therewith;

each of said intermediate members is in the form of a plate-like member that is mounted on a respective shaft that in turn is rotatably mounted on said carrier plate; and in which said free ends of said lever arms of said linkage systems are pivotably supported on said plate-like members; and a potentiometer to determine the position of said measuring element, each of said shafts being connected to said potentiometer that measures rotational movements of that shaft.

7. An apparatus according to claim 6, in which a respective arresting mechanism is operatively associated with each of said intermediate members.

8. In an apparatus for positioning a measuring element, such as a Doppler signal emitter or receiver, for determining the position of a blood vessel and/or the direction in which the blood flows in this blood vessel, with said measuring element being pivotably mounted, via two parallelogram-type linkage systems that are disposed at an angle to one another, in such a way as to be movable in a random manner, the improvement wherein:

said linkage systems have lever arms with free ends that are respectively supported on a common carrier plate including a respective pivotably mounted intermediate member therewith;

each of said intermediate members is in the form of a plate-like member that is mounted on a respective shaft that in turn is rotatably mounted on said carrier plate; and in which said free ends of said lever arms of said linkage systems are pivotably supported on said plate-like members; and arresting mechanisms are operatively associated with said shafts that carry said intermediate members.

9. An apparatus according to claim 8, in which each of said arresting mechanisms is formed by a dual-arm arresting shoe that extends about said shaft.

10. An apparatus according to claim 9, which includes tensioning means for tightening said arresting shoes in common.

11. An apparatus according to claim 10, in which said tensioning means are supported by an abutment means that is fixedly mounted on said carrier plate, and which includes a tightening screw for shifting said tensioning means.

12. An apparatus according to claim 11, in which said tensioning means have a shift path that is adjustable via a stop means that is disposed on said tightening screw and cooperates with said abutment means.

13. An apparatus according to claim 12, in which said stop means is a nut.

* * * * *